(12) United States Patent
Saxena et al.

(10) Patent No.: US 11,119,025 B2
(45) Date of Patent: Sep. 14, 2021

(54) METHOD FOR CHARACTERIZING THE POROSITY OF ROCK

(71) Applicant: SHELL OIL COMPANY, Houston, TX (US)

(72) Inventors: Nishank Saxena, Houston, TX (US); Amie Marie Hows, Houston, TX (US); Ronny Hofmann, Houston, TX (US); Matthias Appel, Houston, TX (US); John Justin Freeman, Pattison, TX (US)

(73) Assignee: SHELL OIL COMPANY, Houston, TX (US)

( * ) Notice: Subject to any disclaimer, the term of this patent is extended or adjusted under 35 U.S.C. 154(b) by 184 days.

(21) Appl. No.: 16/567,197

(22) Filed: Sep. 11, 2019

(65) Prior Publication Data

US 2020/0191698 A1    Jun. 18, 2020

Related U.S. Application Data

(60) Provisional application No. 62/781,019, filed on Dec. 18, 2018.

(51) Int. Cl.
*G06K 9/00* (2006.01)
*G01N 15/08* (2006.01)
(Continued)

(52) U.S. Cl.
CPC ......... *G01N 15/088* (2013.01); *G01N 23/046* (2013.01); *G06T 7/11* (2017.01);
(Continued)

(58) Field of Classification Search
CPC .. G06F 30/20; G06F 2111/10; G06F 2111/08; G06T 7/11; G06T 15/08; G06T 2207/20152; G06T 2207/30108; G06T 7/0004; G06T 7/62; G06T 2207/10081; G06T 2207/20041; G06T 17/05; G06T 2207/10056; G06T 2207/10116;
(Continued)

(56) References Cited

U.S. PATENT DOCUMENTS

2011/0066404 A1* 3/2011 Salazar-Tio ............ G01V 11/00
                                                             703/1
2012/0275658 A1* 11/2012 Hurley ...................... G06T 7/11
                                                             382/109

(Continued)

OTHER PUBLICATIONS

Otsu, "A Threshold Selection Method from Gray-Level Histograms", IEEE Transactions on Systems, Man, and Cybernetics, vol. 9, Issue No. 1, Jan. 1979, pp. 62-66.

(Continued)

*Primary Examiner* — Alex Kok S Liew
(74) *Attorney, Agent, or Firm* — Shell Oil Company (57) ABSTRACT

The present invention provides a method for determining the porosity of rock from a digital image of the rock. A three-dimensional image of a rock is obtained and segmented, and an image porosity is determined from the segmented image of the rock. A porosity correction parameter is obtained from a non-wetting liquid capillary pressure curve derived from the segmented image, and the porosity correction parameter is applied to the image porosity to obtain a corrected porosity of the rock.

9 Claims, 4 Drawing Sheets

(51) Int. Cl.
  *G01N 23/046* (2018.01)
  *G06T 7/11* (2017.01)
  *G06T 7/62* (2017.01)

(52) U.S. Cl.
  CPC ........ *G06T 7/62* (2017.01); *G01N 2015/0846* (2013.01); *G01N 2223/401* (2013.01); *G01N 2223/419* (2013.01); *G01N 2223/616* (2013.01); *G01N 2223/649* (2013.01); *G06T 2207/10116* (2013.01); *G06T 2207/30181* (2013.01)

(58) Field of Classification Search
  CPC ........... G06T 2207/30181; G06T 7/136; G06T 11/60; G06T 2207/10088; G06T 7/44; G01N 23/046; G01N 15/088; G01N 2015/0846; G01N 33/24; G01N 2223/616; G01N 24/081; G01N 2223/305; G01N 2223/401; G01N 2223/419; G01N 2223/649; G01N 23/04; G01N 33/2823; G01N 15/02
  See application file for complete search history.

(56) References Cited

U.S. PATENT DOCUMENTS

| | | | |
|---|---|---|---|
| 2013/0018641 A1* | 1/2013 | Prisco | G06F 30/20 703/9 |
| 2014/0044315 A1 | 2/2014 | Derzhi et al. | |
| 2015/0043787 A1 | 2/2015 | Fredrich et al. | |
| 2018/0121579 A1 | 5/2018 | Fredrich et al. | |

OTHER PUBLICATIONS

Chuang et al., "Fuzzy C-means Clustering With Spatial Information for Image Segmentation", Computerized Medical Imaging and Graphics, vol. 30, Issue No. 1, Jan. 2006, pp. 9-15.

Amabeoku et al. "Evaluation and Application of Digital Rock Physics (DRP) for Special Core Analysis in Carbonate Formations", International Petroleum Technology Conference, Mar. 28, 2013, pp. 26-28, XP055580402.

Saxena et al., "Imaging and Computational Considerations for Image Computed Permeability: Operating Envelope of Digital Rock Physics", Advances in Water Resources, vol. 116, Apr. 4, 2018, pp. 127-144, XP085402086.

Saxena et al., "Rock Properties From Micro-ct Images: Digital Rock Transforms for Resolution, Pore vol. and Field of View", Advances in Water Resources, vol. 134, Sep. 10, 2019, 13 pages, XP085905530.

Sudakov et al., "Driving Digital Rock Towards Machine Learning: Predicting Permeability With Gradient Boosting and Deep Neural Networks", Mar. 16, 2018, pp. 1-15, XP055678933.

Saxena et al., "Estimating Pore vol. of Rocks from Pore-Scale Imaging", Transport in Porous Media, vol. 129, Issue No. 1, May 11, 2019, pp. 403-419.

Zecevic et al., "Progress in Electron Tomography to Assess the 3d Nanostructure of Catalysts", Current Opinion in Solid State and Materials Science, vol. 17, 2013, pp. 115-125.

International Search Report and Written Opinion received for PCT Patent Application No. PCT/US2019/066543, dated Apr. 1, 2020, 13 pages.

\* cited by examiner

METHOD FOR CHARACTERIZING THE POROSITY OF ROCK

CROSS REFERENCE TO EARLIER APPLICATION

This application is a continuation-in-part of U.S. Provisional Application No. 62/781,019, filed Dec. 18, 2018.

FIELD OF THE INVENTION

The present invention relates to a method of characterizing the porosity of rock. In particular, the present invention relates to a method of characterizing the porosity of a rock from a three-dimensional image of the rock.

BACKGROUND OF THE INVENTION

Accurate determination of petrophysical characteristics of rock within a hydrocarbon-containing reservoir is important in determining whether to select the hydrocarbon-containing reservoir for development, as well as developing and managing the hydrocarbon-containing reservoir. For example, underestimating the porosity of the rock of a hydrocarbon-containing formation may lead to significant underestimation of fluid contained in the formation, and, in a worst-case scenario, lead to a decision not to develop a formation that actually contains substantial quantities of hydrocarbons.

Traditionally, petrophysical characteristics of hydrocarbon-containing formation rock have been determined by physical testing of rock samples. Such tests, however, require substantial time and are quite expensive. Further, the number of samples that may be processed is relatively limited due to the time and expense required to conduct each test.

Digital rock physics is a technology that has been developed to provide faster, more, and less expensive analysis of hydrocarbon-containing formation rocks to determine key petrophysical characteristics of the rocks. Digital rock physics utilizes digital images of formation rocks to simulate rock multiphysics at the pore scale and predict properties of complex rocks.

Porosity is among the most fundamental of rock properties, and is utilized to determine the fluid capacity of a hydrocarbon-containing formation and to calculate further rock properties such as permeability. Current digital rock physics technologies determine the porosity of a rock sample by capturing a three-dimensional image of the rock, for example by 3-D x-ray computer tomography, segmenting the resulting image into solid and void space voxels utilizing various image segmentation algorithms, and calculating the porosity of the rock from the total number of void space voxels relative to the total overall number of voxels.

Figure 1:
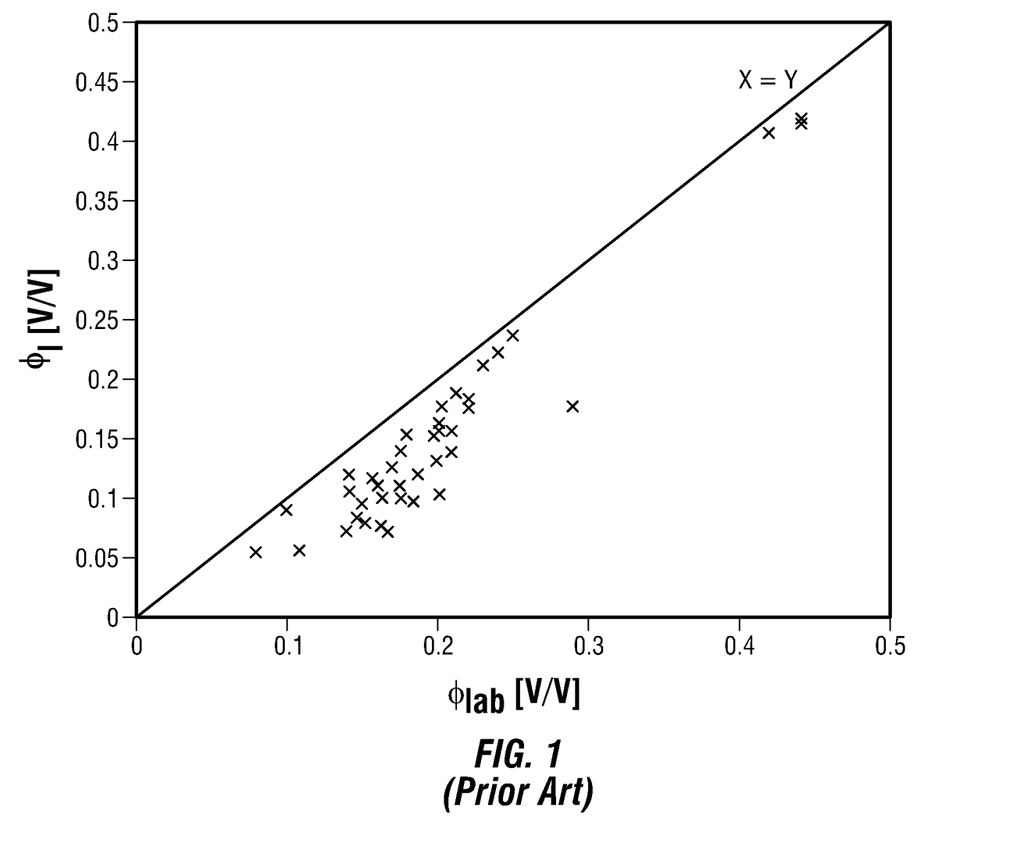
FIG. 1 is a graph showing a plot of laboratory measured porosity of rocks v. the porosity as determined by digital rock image methods of the prior art.

Current digital rock physics methods for determining the porosity of a rock, however, exhibit a significant systematic offset between laboratory measurements of porosity and porosity computed using the digital rock physics models, where the porosity computed using the digital rock physics models is consistently significantly underestimated relative to the porosity as measured by laboratory measurements (the "true" porosity). This offset is shown graphically in FIG. 1 where porosity computed using conventional digital rock physics models ($\varphi_I$) is plotted against laboratory measured "true" porosity ($\varphi_{lab}$). The digital rock physics models consistently underestimate the porosity relative to true porosity as measured in laboratory testing as shown by the digital rock physics calculated porosities consistently falling below the x=y slope at which image modelled porosity would equal laboratory measured true porosity.

This bias cannot be accounted for by differences in rock microstructures generated by various segmentation algorithms since such differences are relatively minor as long as all phases are segmented consistently. As such, current digital rock methods are relatively inaccurate and underestimate the true porosity of hydrocarbon-containing formation rock.

An improved digital rock physics method is desirable which will more accurately estimate the porosity of hydrocarbon-containing formation rock from a three dimensional image of the rock.

SUMMARY OF THE INVENTION

The present invention is directed to a method for estimating the porosity of a rock, comprising:

obtaining a three-dimensional image of a rock wherein the image is comprised of a plurality of voxels and the image has a resolution;

processing the three-dimensional image of the rock to segment the image by selecting each voxel of the image to represent either pore space in the rock or solid material in the rock;

determining an image porosity of the rock from the segmented three-dimensional image of the rock;

determining a non-wetting liquid capillary pressure curve from the segmented three-dimensional image of the rock;

determining a pore geometric factor from the non-wetting liquid capillary pressure curve;

determining a pore throat resolution factor from the non-wetting liquid capillary pressure curve and the resolution of the image;

utilizing the pore geometric factor and the pore throat resolution factor to determine a porosity correction parameter;

applying the porosity correction parameter to the image porosity of the rock to obtain a corrected porosity of the rock.

DETAILED DESCRIPTION OF THE INVENTION

The present invention provides a method for accurately determining the porosity of a rock based on an original three dimensional pore-scale image of the rock having limited resolution relative to the actual pore structure of the rock. It has been found that, contrary to current assumptions in digital rock physics modelling, that a substantial fraction of the pore volume of hydrocarbon-containing rocks is contained in pores of a size below the image resolution provided by three dimensional pore-scale imaging technology commonly used to provide images of such rocks. As a result, conventional digital rock physics modelling substantially underestimates the porosity of hydrocarbon-containing rocks by failing to account for pores that are smaller than the image resolution of the pore-scale imaging technology.

The present invention provides a method for determining the porosity of a hydrocarbon-containing rock based upon a three dimensional digital image provided by pore-scale imaging technology, where the porosity determined in accordance with the present method includes the porosity provided by pores having a size below the image resolution of the image. The relation between the fraction of porosity that is visible in an image and the total porosity is determined using the seemingly unrelated physical mechanism of capillary pressure in rocks. Capillary pressure is the pressure difference across the interface between two immiscible fluids in a constricted channel (e.g. air and a non-wetting liquid such as mercury). Non-wetting liquid injection capillary pressure curves describe the relation between the pressure applied on the non-wetting liquid to overcome capillary pressure and thereby enter pore throats and the fractional bulk volume of the rock that is occupied by the non-wetting liquid at that pressure. The total porosity of a hydrocarbon-containing rock may be determined by utilizing capillary pressure curves based on an image of a rock to determine a correction factor to be applied to porosity determined from visible pores in the image, where the correction factor accounts for pores having a size below the image resolution of the image.

In the method of the invention, the petrophysical characteristics of a rock, particularly the porosity of the rock, are determined. In a preferred embodiment, the rock may be a rock from any hydrocarbon-containing formation, or a portion of a hydrocarbon-containing formation, for which the petrophysical characteristics of the formation, or portion thereof, are of interest. Preferably, the rock may be a sandstone or a carbonate from a hydrocarbon-containing formation. The rock may also be a shale from a hydrocarbon-containing formation. The rock may be obtained by conventional means for obtaining rock samples from a hydrocarbon formation. In a preferred embodiment, a core sample of the rock is obtained by coring a portion of the formation from within a well in the formation. Alternatively, a sample of the rock may be obtained from drill cuttings produced in drilling a well in the formation.

The rock sample should be of sufficient size to obtain a three-dimensional image of sufficient volume at the scale that the image is generated. In particular, the rock sample should be of sufficient size such that porosity provided by pores within the bulk of the sample is substantially greater than porosity provided by pores at the edge of the sample at the scale or field of view of the image to be generated.

A three-dimensional image comprised of a plurality of voxels is obtained from the rock sample. The three-dimensional image of the rock may be obtained utilizing pore-scale imaging technology. A three-dimensional image of the rock may be obtained by X-ray micro-computed tomography (micro-CT), x-ray nano-computed tomography (nano-CT), acoustic microscopy, or magnetic resonance imaging. Most preferably the three-dimensional image of the rock is obtained by micro-CT to provide sufficient field of view of the rock to avoid edge pores distorting the overall porosity and pore throat size of the resulting image, as well as to reduce scanning time and computational requirements that higher resolution tomography (e.g. nano-CT) would require.

The three-dimensional image of the rock obtained by pore-scale imaging technology has a resolution. The voxels of the three-dimensional image define the resolution of the image. The image is comprised of a plurality of voxels, where the volume defined by each voxel represents a maximum resolution of the image. The resolution of the image should be selected to provide a voxel size at which the dominant pore throats for fluid flow in the rock are sufficiently resolved and at which a sufficient field of view is provided so as to be representative of the whole rock for a given petrophysical property to be analyzed (e.g. porosity). For purposes herein, the dominant pore throat size is the size of pore throats of pores that a non-wetting liquid enters at the pore entry pressure, where the pore entry pressure is the minimum pressure required before the non-wetting liquid can begin to invade the pore structure of the rock.

The resolution of a micro-CT image may be chosen based on the size of the rock sample, the relative average pore size of the type of rock, the time required for the imaging, and the computational power required to store and conduct further computational activity on the image data. The image resolution is chosen to be detailed enough that a non-wetting liquid capillary injection curve can be plotted based on a segmented image produced from the image while maintaining a sufficient field of view to avoid edge pores distorting the overall porosity and pore throat size of the resulting image. In a preferred embodiment, the image resolution is selected to require as little computational power to store and conduct further computational activity on the image while providing sufficient detail to construct a capillary injection curve based on the segmented image. The image resolution may be selected based on the type of rock, where sandstones generally have a larger pore structure than carbonates, and require less image resolution than carbonates, and carbonates have a larger pore structure than shales, and require less image resolution than shales. The resolution of the micro-CT image may range from 0.1 $\mu m^3$ to 30 $\mu m^3$ per voxel. For sandstones, the micro-CT image preferably is produced at a resolution of from 1 $\mu m^3$ to 25 $\mu m^3$ per voxel, or from 2.5 $\mu m^3$ to 15 $\mu m^3$ per voxel; for carbonates the resolution of the micro-CT image may range from 0.5 $\mu m^3$ to 20 $\mu m^3$, or from 1 $\mu m^3$ to 10 $\mu m^3$; and for shales the resolution of the micro-CT (or nano-CT) image may range from 0.1 $\mu m^3$ to 10 $\mu m^3$, or from 0.5 $\mu m^3$ to 5 $\mu m^3$.

In a preferred embodiment, the acquired image may be processed to reduce noise and image artifacts. Noise may be filtered from the acquired image by filtering using a local means filter to reduce noise. Imaging artifacts, predominant at the outer edges of the acquired image, may be reduced by processing the image while excluding the outer edges of the image.

The three-dimensional image obtained of the rock is processed to segment the voxels of the image into voxels representing either pore space in the rock or solid material in the rock, thereby producing a binary image in which pore voxels have a value of 0 and solid material voxels have a value of 1 (or vice versa). The image obtained of the rock may be a grayscale image, and processing the voxels of the image to segment the image into voxels representing pore space or solid material may be effected by assigning a voxel a designation as pore space or as solid material based on a threshold, wherein voxels having an image intensity above the threshold may be assigned a value representing a pore (or solid material) and voxels having an image intensity below the threshold may be assigned a value representing solid material (or a pore). A threshold may be calculated using Otsu's method as described in Otsu, N., *A Threshold Selection Method from Gray-level Histogram*, IEEE pp. 62-66, Trans. SMC-9 (1979).

The three-dimensional image of the rock may be processed to segment the voxels into pore space voxels and solid material voxels utilizing segmentation algorithms known in the art. In one embodiment, the image may be segmented using a fuzzy c-means clustering algorithm in accordance with the method as described in Chuang, K.-S., Tzeng, H.-L., Chen, S., Wu, J., Chen, T.-J. *Fuzzy C-Means Clustering with Spatial Information for Image Segmentation*, Comput. Med. Imaging Graph., 30, 9-15 (2006). In another embodiment, the image may be segmented using an Otsu algorithm. Segmentation using segmentation algorithms is preferably conducted automatically using data processing systems.

After the image has been segmented, an image porosity of the rock is determined from the segmented three-dimensional image of the rock. The image porosity of the rock may be estimated by summing the number of voxels in the segmented image that represent pore space, summing the total number of voxels in the segmented image (or obtaining the total number of voxels from the imaging parameters), then dividing the sum of the number of voxels in the segmented image that represent pore space by the total number of voxels in the segmented image. A sum of the number of voxels in the segmented image that represent pore space may be determined by adding up the number of voxels assigned a binary value (e.g. 1 or 0) representing pore space. A sum of the total number of voxels in the segmented image may be determined by adding up the total number of voxels assigned a binary value, both pore space voxels and solid material voxels.

A correction factor is determined from the segmented three-dimensional image to correct the image porosity of the rock to obtain a corrected porosity of the rock. The relation between the image porosity ($\varphi_I$), true porosity ($\varphi_\infty$), and the correction factor ($\alpha$) may be expressed as follows:

$$\varphi_I = \alpha \varphi_\infty \text{ where } 0 < \alpha < 1. \qquad (1)$$

Figure 2:
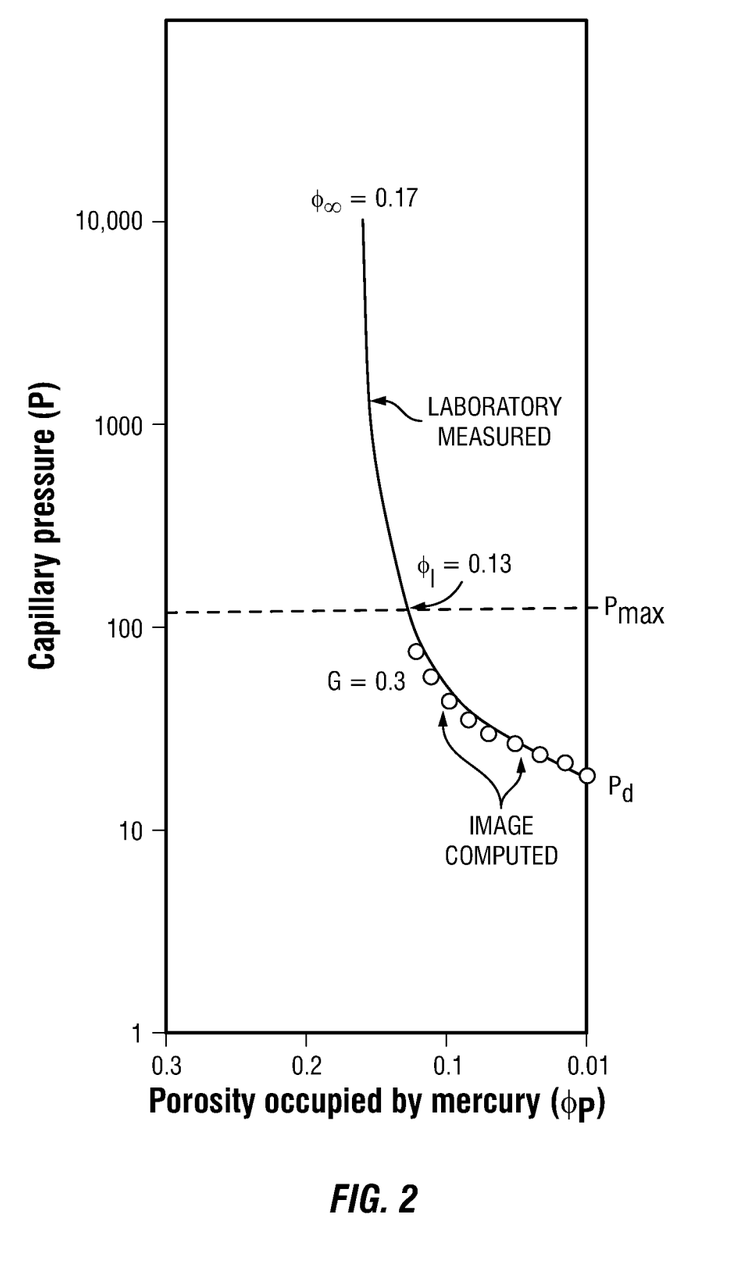
FIG. 2 is a mercury capillary pressure curve simulated from a digital rock image (porosity occupied by mercury v. pressure).

In order to determine the correction factor, first a non-wetting liquid capillary pressure curve is determined from the segmented three-dimensional image of the rock for pores distinguishable in the segmented image at pressures up to an image-limited pressure. Preferably mercury or Wood's metal is selected as the non-wetting liquid. A non-wetting liquid capillary pressure curve may be determined from the segmented image by plotting the porosity of the rock occupied by the non-wetting liquid at selected pressures up to the image-limiting pressure based upon simulations of the non-wetting liquid filling the pore space of the image. To simulate the non-wetting liquid filling the pore space of the image, the pore throat size penetrated at a given pressure may be determined according to the Young-Laplace equation:

$$D = 4\sigma \cos \theta / P \qquad (2)$$

Where P is the given pressure, $\sigma$ is the non-wetting liquid-air surface tension (480 dyne/cm for mercury-air), $\theta$ is the contact angle (140° for mercury) and D is the pore throat size penetrated at the given pressure. To evaluate the porosity of the rock occupied by a non-wetting liquid at a given pressure, a simulation may be conducted in which voxels of pore space of pore bodies having a pore throat size of D or larger are assumed to be filled with the non-wetting liquid at the given pressure, the voxels that are "filled" with the liquid are summed, and the porosity of the rock occupied by the non-wetting liquid is calculated by dividing the sum of the number of pore space voxels filled with liquid by the total number of voxels in the image. As shown in FIG. 2, the porosity of the rock occupied by the non-wetting liquid may then plotted against the given pressure for a number of selected given pressures above the entry pressure ($P_d$) up to the image-limited pressure ($P_{max}$). The entry pressure ($P_d$) is the pressure at which the non-wetting liquid initially enters pores in the rock, and the image-limited pressure ($P_{max}$) is the minimum pressure required to overcome the capillary pressure of the narrowest pore throat distinguishable in the segmented image.

Thomeer's model of the Capillary Pressure Curve provides that:

$$\varphi_P = \varphi_\infty (e^{-G/Log\ 10(N)}) \qquad (3)$$

where $\varphi_P$ is the porosity of the rock occupied by a non-wetting liquid at pressure P, $\varphi_\infty$ is the porosity of the rock occupied by a non-wetting liquid at infinite pressure (the true porosity since the pressure is sufficient to force the non-wetting liquid through the smallest pore throat in the rock), G is the pore geometric factor reflecting the distribution of pore throats and their associated pore bodies' volume, and N is the pore throat resolution factor. When P is equal to the image-limiting pressure, then $$\varphi_I = \varphi_\infty (e^{-G/Log\ 10(N)}) \qquad (4)$$

and the porosity correction factor $\alpha = (e^{-G/Log\ 10(N)})$. The porosity correction factor $\alpha$, therefore, can be determined from the pore geometric factor G and the pore resolution factor N.

In the method of the present invention, the pore resolution factor N is determined from the non-wetting liquid capillary pressure curve derived from the image and the image resolution as determined from the size of the voxels. The pore resolution factor N is the ratio of the pore throat size ($D_d$) entered by the non-wetting liquid at the entry pressure ($P_d$) to the size of the voxels ($\Delta x$), $N = (D_d / \Delta x)$. The size of the voxels may be determined from the parameters of the three-dimensional imaging (i.e. the resolution of the image). The pore throat size ($D_d$) of pores entered by the non-wetting liquid at entry pressure ($P_d$) may be determined from the non-wetting liquid capillary pressure curve derived from the segmented three-dimensional image of the rock according to the equation:

$$D_d = 4\sigma \cos \theta / P_d \qquad (5).$$

In the method of the present invention, the pore geometric factor G is determined from the non-wetting liquid capillary pressure curve derived from the image. The pore geometric factor G may be determined by plotting a best fit curve to the non-wetting liquid capillary pressure curve simulated from the segmented image and determining the pore geometric factor from the shape of the curve. The best fit curve may be plotted by the least squares method or by any conventional curve-fitting method.

As described above, the pore geometric factor G and the pore throat resolution factor N are utilized to determine the porosity correction factor. The porosity correction factor $\alpha$ may be calculated from the pore geometric factor G and the pore throat resolution factor N according to the equation:

$$\alpha = (e^{-G/Log\ 10(N)}) \quad (6).$$

The porosity correction factor $\alpha$ is then applied to the image porosity of the rock to obtain a corrected porosity. The corrected porosity ($\varphi_\infty$) may be determined from the image porosity ($\varphi_I$) of the rock and the porosity correction factor ($\alpha$) according to the following equation:

$$\varphi_I/\alpha = \varphi_\infty \quad (7)$$

The corrected porosity is substantially the same as the true porosity.

Example 1

The corrected porosity of a sandstone from a hydrocarbon-containing formation was determined in accordance with the method of the present invention and was compared with the true porosity of the sandstone as determined by physical measurements.

A core sample of sandstone was recovered from a hydrocarbon-containing formation. The true porosity of the sandstone was determined in accordance with the industry standard method of gas expansion using a helium porosimeter. The true porosity of the sandstone sample was found to be 0.17.

The porosity of the sandstone was then determined by digital rock imaging in accordance with the method of the present invention. A sample of sandstone rock was three-dimensionally imaged by micro-CT imaging at ambient temperature at a resolution of 2.07 µm (e.g. 1 voxel of the image=2.07 µm³) at a total rock sample image of 1300×1300×1300 voxels (2.197 billion voxels). The resulting three-dimensional micro-CT image was then processed to segment the image into pore space voxels and solid material voxels using a Fuzzy C-Means clustering algorithm. The image porosity was determined from the segmented three-dimensional image of the rock by summing the number of voxels representing pore space in the segmented image and dividing by the total number of voxels in the image as determined from the imaging parameters (2.197 billion voxels). The image porosity was calculated to be 0.14.

A mercury capillary injection curve was then determined from the segmented three-dimensional image of the rock. An image-based curve was created by plotting the fractional bulk volume of the segmented rock image occupied by mercury against pressure in accordance with the Young-Laplace equation (P=4σ cos θ/D, P=pressure, D=pore throat size penetrated at a given pressure P, σ=the mercury liquid-air surface tension (480 dyne/cm), and θ=the contact angle (140°)) where voxels of pore space of pore bodies having a pore throat size of D or larger are assumed to be filled with mercury at the given pressure. Table 1 provides the calculated fractional bulk volume occupied by mercury at selected pressures as determined from the segmented three-dimensional image.

TABLE 1

| P (psi) | Fract. BV (v/v) |
|---|---|
| 1.89 | 0 |
| 2.21 | 0 |
| 2.64 | 0 |
| 3.36 | 0 |
| 4.34 | 0 |
| 5.4 | 0 |
| 7.28 | 0 |
| 9.42 | 0 |
| 11.26 | 0.01 |
| 12.43 | 0.01 |
| 12.68 | 0.01 |
| 13.18 | 0.02 |
| 13.71 | 0.03 |
| 15.14 | 0.04 |
| 16.35 | 0.07 |
| 17.69 | 0.08 |
| 19.89 | 0.11 |
| 21.54 | 0.11 |
| 24.25 | 0.11 |
| 26.76 | 0.12 |
| 30.14 | 0.13 |
| 36.02 | 0.13 |
| 42.21 | 0.14 |
| 53.36 | 0.14 |

Figure 3:
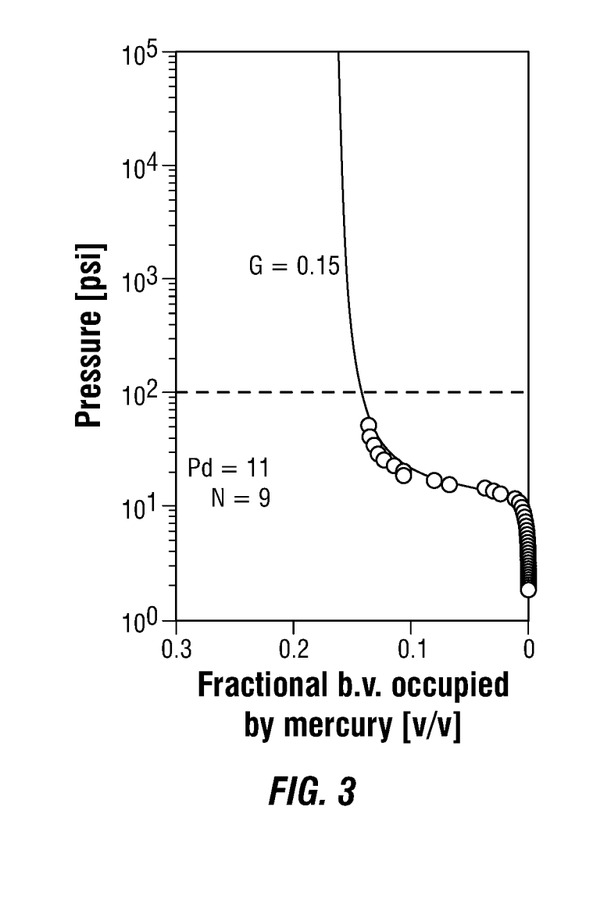
FIG. 3 is a mercury capillary pressure curve simulated from a digital rock image of a first sandstone rock sample in accordance with a method of the present invention (fractional bulk volume occupied by mercury [porosity] v. pressure).

The resulting curve is shown in FIG. 3.

A pore throat resolution parameter N was determined from the mercury capillary injection curve and the voxel size. The pore throat size entered by mercury at the entry pressure ($D_d$) was determined from the mercury capillary injection curve and the Young-Laplace equation, where the entry pressure ($P_d$) was 11.26 psi as shown in Table 1, and the pore throat size at the entry pressure was $D_d = 4\sigma \cos\theta/P_d = 19.4$ µm. The voxel size ($\Delta x$) was the resolution of the image=2.07 µm. The pore throat resolution parameter $N = D_d/\Delta x = 9$.

A pore geometric factor G was determined from the mercury capillary injection curve by curve fitting with a least square curve fitting, with higher weight given to pores that are better resolved in the image. G was determined to be 0.15 from the mercury capillary injection curve.

The pore throat resolution parameter N and the pore geometric factor G were then used to determine a porosity correction factor $\alpha$ according to the equation $\alpha = e^{-G/Log\ 10(N)}$. Utilizing N=9 and G=0.15, the porosity correction factor $\alpha$ was calculated to be 0.823.

Applying the corrected porosity factor $\alpha$ to the image porosity, the corrected porosity may be obtained according to the equation $\varphi_I/\alpha = \varphi_\infty$. Calculating the corrected porosity from the image porosity of 0.14 and the porosity correction factor $\alpha$ of 0.823, the corrected porosity was determined to be 0.17.

The corrected porosity of the rock sample determined by the method of the present invention, 0.17, was found to be the same as the true porosity of the rock sample as measured in accordance the gas expansion method. Further, the porosity determined from the image itself, without correction, underestimated the true porosity by about 18% by volume.

Example 2

The porosity of a sandstone rock from a different, second, hydrocarbon-containing formation than examined in the first Example above was determined in accordance with the method of the present invention and was compared with the true porosity of the sandstone rock as determined by physical measurements.

A core sample of sandstone rock was recovered from the second hydrocarbon-containing formation. The true porosity of the sandstone rock was determined in accordance with the industry standard method of gas expansion using a helium porosimeter. The true porosity of the sandstone rock sample was found to be 0.14.

The porosity of the sandstone was then determined by digital rock imaging in accordance with the method of the present invention. A sample of sandstone rock was three-dimensionally imaged by micro-CT imaging at ambient temperature at a resolution of 2.07 µm (e.g. 1 voxel of the image=2.07 µm$^3$) at a total rock sample image of 1300×1300×1300 voxels (2.197 billion voxels). The resulting three-dimensional micro-CT image was then processed to segment the image into pore space voxels and solid material voxels using a Fuzzy C-Means clustering algorithm. The image porosity was determined from the segmented three-dimensional image of the rock by summing the number of voxels representing pore space in the segmented image and dividing by the total number of voxels in the image as determined from the imaging parameters (2.197 billion voxels). The image porosity was calculated to be 0.10.

A mercury capillary injection curve was then determined from the segmented three-dimensional image of the rock. An image-based curve was created by plotting the fractional bulk volume of the segmented image occupied by mercury against pressure in accordance with the Young-Laplace equation (P=4σ cos θ/D, P=pressure, D=pore throat size penetrated at a given pressure P, σ=mercury liquid-air surface tension (480 dyne/cm), and θ=contact angle (140°)) where voxels of pore space of pore bodies having a pore throat size of D or larger are assumed to be filled with mercury at the given pressure. Table 2 provides the calculated fractional bulk volume occupied by mercury at selected pressures as determined from the segmented three-dimensional image.

TABLE 2

| P (psi) | Fract. BV (v/v) |
|---------|-----------------|
| 1.64    | 0               |
| 2.99    | 0               |
| 13.53   | 0               |
| 25.56   | 0               |
| 29.97   | 0.01            |
| 32.45   | 0.01            |
| 35.14   | 0.02            |
| 36.56   | 0.04            |
| 39.59   | 0.05            |
| 42.87   | 0.08            |
| 52.3    | 0.08            |

Figure 4:
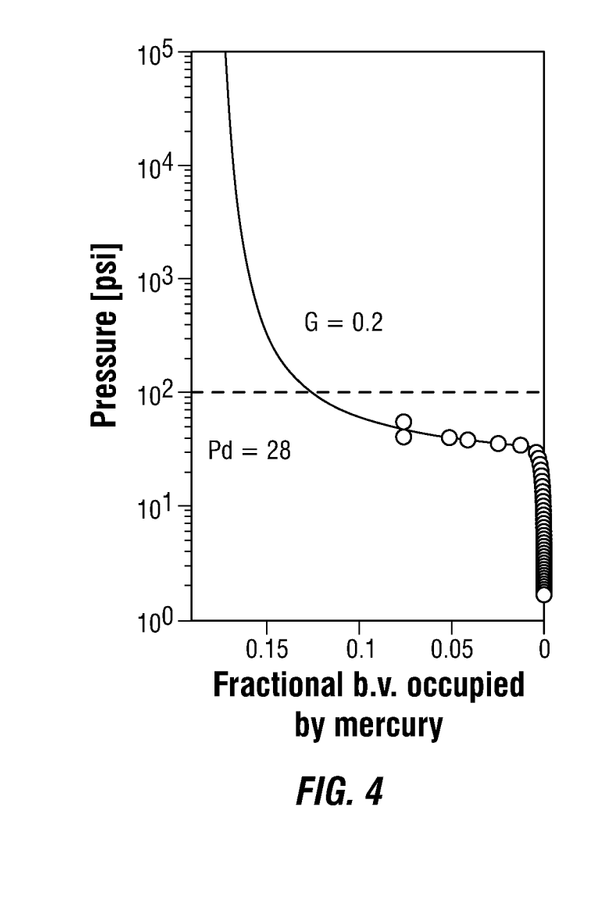
FIG. 4 is a mercury capillary pressure curve simulated from a digital rock image of a second sandstone rock sample in accordance with a method of the present invention (fractional bulk volume occupied by mercury [porosity] v. pressure).

The resulting curve is shown in FIG. 4.

A pore throat resolution parameter N was determined from the mercury capillary injection curve and the voxel size. The pore throat size entered by mercury at the entry pressure ($D_d$) was determined from the mercury capillary injection curve and the Young-Laplace equation, where the entry pressure ($P_d$) was 28 psi and the pore throat size at the entry pressure was $D_d$=4σ cos θ/$P_d$=7.86 µm. The voxel size (Δx) was the resolution of the image=2.07 µm. The pore throat resolution parameter N=$D_d$/Δx=3.8.

A pore geometric factor G was determined from the mercury capillary injection curve by curve fitting with a least square curve fitting, with higher weight given to pores that are better resolved in the image. G was determined to be 0.2 from the mercury capillary injection curve.

The pore throat resolution parameter N and the pore geometric factor G were then used to determine a porosity correction factor α according to the equation $\alpha = e^{-G/Log\ 10(N)}$. Utilizing N=3.8 and G=0.2, the porosity correction factor α was calculated to be 0.714.

Applying the porosity correction factor α to the image porosity ($\varphi_I$), the corrected porosity ($\varphi_\infty$) may be obtained according to the equation $\varphi_I/\alpha = \varphi_\infty$. Calculating the corrected porosity from the image porosity of 0.10 and the porosity correction factor α of 0.714, the corrected porosity was determined to be 0.14.

The corrected porosity of the rock sample determined by the method of the present invention, 0.14, was found to be the same as the true porosity of the rock sample as measured in accordance the gas expansion method. Further, the porosity determined from the image itself, without correction, underestimated the true porosity by about 29% by volume.

Example 3

Figure 5A:
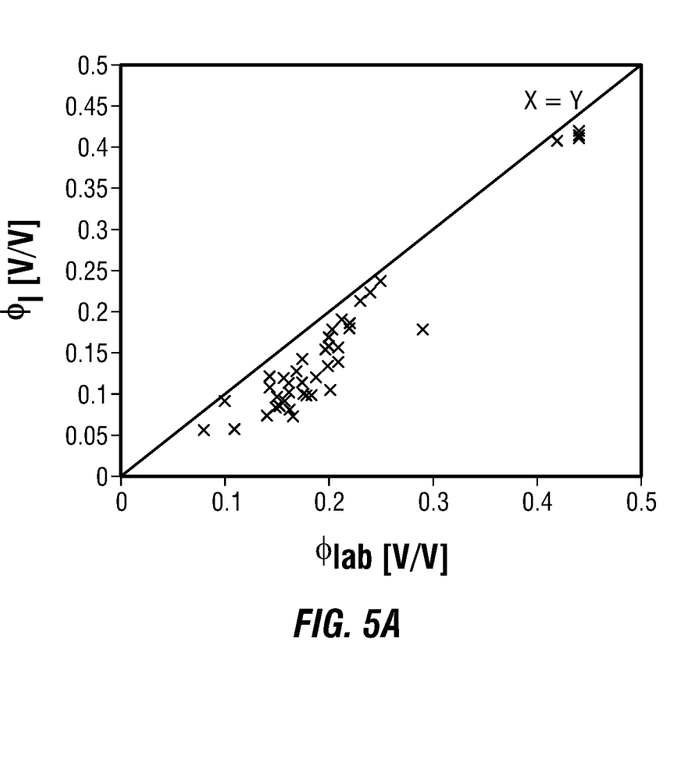
FIG. 5A is a graph showing a plot of laboratory measured porosity of rocks v. an uncorrected porosity as determined by digital rock image methods
Figure 5B:
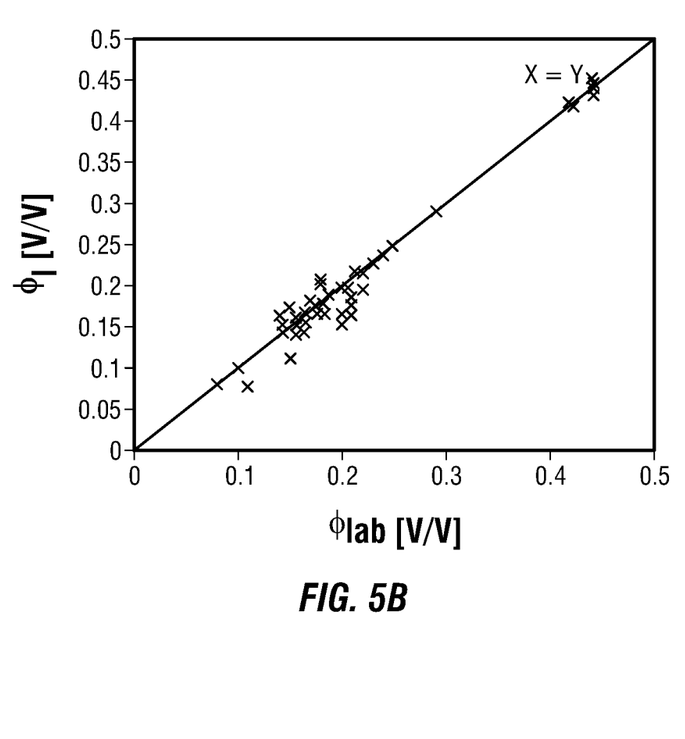
FIG. 5B is a graph showing a plot of laboratory measured porosity of rocks v. a corrected porosity as determined by a digital rock image in accordance with a method of the present invention.

The true porosity, as determined in accordance with the industry standard method of gas expansion using a helium porosimeter, the image porosity, and a corrected image porosity determined is described above in Examples 1 and 2 and in accordance with the method of the present invention were measured and calculated for several samples of rock. Plots of the image porosity v. true porosity and corrected image porosity v. true porosity were prepared based on these measurements and calculations, and are shown in FIG. 5. The plots in FIG. 5 include the x=y slope line at which the image porosity would be equal to the true porosity. As shown by comparing the plot of the image porosity v. true porosity and the plot of corrected image porosity v. true porosity as against the x=y slope, the corrected image porosities were substantially the same as the true porosity while the image porosities consistently significantly underestimated the true porosity of the rock.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A method for estimating the porosity of rock, comprising:
   obtaining a three-dimensional image of a rock wherein the image is comprised of a plurality of voxels and the image has a resolution;
   processing the three-dimensional image of the rock to segment the image by selecting each voxel of the image to represent either pore space in the rock or solid material in the rock;
   determining an image porosity of the rock from the segmented three-dimensional image of the rock;
   deriving a non-wetting liquid capillary pressure curve from the segmented three-dimensional image of the rock;
   determining a pore geometric factor from the non-wetting liquid capillary pressure curve;
   determining a pore throat resolution factor from the non-wetting liquid capillary pressure curve and the resolution of the image;
   utilizing the pore geometric factor and the pore throat resolution parameter to determine a porosity correction parameter;
   applying the porosity correction parameter to the image porosity of the rock to obtain a corrected porosity of the rock.

2. The method of claim 1, wherein the three-dimensional image of the rock is obtained by x-ray computer tomography.

3. The method of claim 1, wherein the rock is obtained from a hydrocarbon-bearing formation and is comprised of sandstone.

4. The method of claim 1, wherein the rock is obtained from a hydrocarbon-bearing formation and is comprised of carbonate.

5. The method of claim 1, wherein the rock is obtained from a hydrocarbon-bearing formation and is comprised of shale.

6. The method of claim 1, wherein the non-wetting liquid is mercury.

7. The method of claim 1, wherein the non-wetting liquid capillary pressure curve is derived from the segmented three-dimensional image of the rock at pressures of up to an image-limited pressure, where the image-limited pressure is the minimum pressure that can be applied on the non-wetting liquid to overcome the capillary pressure of the narrowest pore throat distinguishable from the segmented three-dimensional image of the rock.

8. The method of claim 1, wherein the pore geometric factor is determined from the non-wetting liquid capillary pressure curve by plotting a best fit curve to the non-wetting liquid capillary pressure curve and determining the pore geometric factor from the shape of the curve.

9. The method of claim 1, wherein the pore throat resolution factor is determined by determining a pore throat size of pores entered by the non-wetting liquid at an entry pressure from the non-wetting liquid capillary pressure curve and calculating a ratio between the pore throat size of pores entered by the non-wetting liquid at the entry pressure and the resolution of the image.

* * * * *